(12) United States Patent
Huxel et al.

(10) Patent No.: US 6,423,332 B1
(45) Date of Patent: Jul. 23, 2002

(54) METHOD AND COMPOSITION FOR DEFORMING SOFT TISSUES

(75) Inventors: Shawn T. Huxel, Lawrenceville; Ram L. Kataria, Hamilton Square; Joel S. Rosenblatt, Watchung, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/579,214

(22) Filed: May 26, 2000

(51) Int. Cl.$^7$ ................................................. A61F 13/00
(52) U.S. Cl. .................. 424/422; 424/484; 424/486; 424/487; 424/489; 424/78.08; 424/78.17; 424/78.24
(58) Field of Search ................................ 424/422, 484, 486, 487, 78.08, 78.17, 78.24; 514/944

(56) References Cited

U.S. PATENT DOCUMENTS

| | | | |
|---|---|---|---|
| 3,419,006 A | 12/1968 | King | |
| 3,971,376 A | 7/1976 | Wichterle | |
| 4,134,871 A | 1/1979 | Otani et al. | |
| 4,197,846 A | 4/1980 | Bucalo | |
| 4,272,518 A | 6/1981 | Moro et al. | |
| 4,404,183 A | 9/1983 | Kawata et al. | |
| 4,423,099 A | 12/1983 | Mueller et al. | |
| 4,527,293 A | 7/1985 | Eckstein et al. | |
| 4,698,373 A | 10/1987 | Tateosian et al. | |
| 4,773,393 A | 9/1988 | Haber et al. | |
| 4,777,200 A | 10/1988 | Dymond et al. | |
| 4,803,075 A | 2/1989 | Wallace et al. | |
| 4,828,827 A | * 5/1989 | Henderson et al. | ............ 424/80 |
| 4,828,828 A | 5/1989 | Trager et al. | |
| RE32,969 E | 6/1989 | Trager et al. | |
| 5,007,940 A | 4/1991 | Berg | |
| 5,067,965 A | 11/1991 | Ersek et al. | |
| 5,143,724 A | 9/1992 | Leshchiner et al. | |
| 5,162,430 A | 11/1992 | Rhee et al. | |
| 5,258,028 A | 11/1993 | Ersek et al. | |
| 5,330,768 A | 7/1994 | Park et al. | |
| 5,336,263 A | 8/1994 | Ersek et al. | |
| 5,399,351 A | * 3/1995 | Leshchiner et al. | ......... 424/422 |
| 5,514,754 A | 5/1996 | Henderson et al. | |
| 5,813,411 A | 9/1998 | Van Bladel et al. | |
| 5,840,329 A | 11/1998 | Bai | |
| 5,902,832 A | * 5/1999 | Van Bladel et al. | ........ 514/944 |

FOREIGN PATENT DOCUMENTS

| | | |
|---|---|---|
| EP | 0251695 A2 | 2/1989 |
| EP | 0684045 A1 | 11/1995 |
| EP | 0730847 A1 | 9/1996 |
| EP | 0826381 A2 | 3/1998 |
| WO | WO 86/01813 A2 | 3/1986 |
| WO | WO 93/16658 A1 | 9/1993 |
| WO | WO 93/19702 A1 | 10/1993 |
| WO | WO 94/02184 A1 | 2/1994 |
| WO | WO 94/21299 A1 | 9/1994 |
| WO | WO 98/56431 A1 | 12/1998 |

OTHER PUBLICATIONS

U.S. application No. 09/579,214, Huxel et al., filed May 26, 2000.

\* cited by examiner

Primary Examiner—Thurman K. Page
Assistant Examiner—Liliana Di Nola-Baron

(57) ABSTRACT

The present invention provides a composition and method for augmenting soft tissue, which composition includes a continuous phase that is a solid at temperatures less than about 10° C. or greater than about 30° C. and is a fluid at temperatures between about 10° C. and about 30° C., and which contains an aqueous solvent having dissolved therein a hydrogel and a dehydrating agent, and a discontinuous phase containing a plurality of hydrophilic hydrogel particles that are swellable in the aqueous solvent, that are not biodegradable for periods of time in excess of one year, and that have a hydrated diameter of greater than about 25 microns upon hydration by physiologic fluid; wherein the final volume of the hydrophilic hydrogel particles upon hydration by physiologic fluid is substantially the same as the initial volume of the composition used to augment the soft tissue.

17 Claims, No Drawings

METHOD AND COMPOSITION FOR DEFORMING SOFT TISSUES

FIELD OF THE INVENTION

The invention relates to compositions that are used in methods of deforming a selected tissue structure for treatment of e.g., incontinence, vesicoureteral reflux, or gastroesophageal reflux.

BACKGROUND OF THE INVENTION

In the recent past, urinary incontinence has been successfully treated by using minimally invasive surgical means. One method which has been used to treat patients with urinary incontinence is periurethral or transurethral injection of a composition commercially sold in Canada as "Polytef" and as "Urethrin." "Polytef" is a paste comprising a fifty-fifty (50/50) by weight mixture of glycerine liquid and PTFE particles. However, after injection, over a period of time the glycerin is readily dissipated into the body and then metabolized or eliminated, leaving only the PTFE particles. This means that only fifty (50) percent of the injected weight remains at the injection site. Consequently the surgeon must inject significantly more volume than necessary and at times may inadvertently coapt the urethra further than is desired. This closure could possibly be complete and thus place the patient into temporary urinary retention. Additionally, the fact that a large portion of the injected volume disappears makes it difficult for the surgeon to visually gauge how much is an appropriate amount of the PTFE paste to inject. As a result, the surgeon is likely not to inject enough paste volume. The procedure therefore may fail, and multiple procedures to inject additional paste may be required. An additional drawback of the PTFE paste is that the PTFE particle size is sufficiently small so as to allow the particles to migrate to other locations of the body such as the lungs, brain, etc. PTFE particles have been known to induce tissue reaction and form PTFE-induced granulomas in certain individuals. This tissue reaction to PTFE has caused concerns for the patient's safety. Also, the PTFE paste is highly viscous and can only be injected by applying a large injection force (IF). Often this is accomplished by utilizing an injection assist device in order to deliver the highly viscous PTFE paste through a needle of any acceptable size at acceptable flow rates.

An alternative to using the PTFE paste is using a collagen suspension. The collagen suspension is injected in the same manner as PTFE paste so as to form a fibrous mass of tissue around the augmentation site. This fibrous mass created by the collagen injection, however, decreases in size and breaks down over time as it is eventually degraded by the patient's body. As a result, additional injections are periodically required.

Another alternative is to inject silicone particles dispersed in an aqueous, polyvinylpyrrolidone (PVP) solution. This combination has the same problems as the PTFE paste, in that the polyvinylpyrrolidone solution is readily dissipated away from the area of injection, leaving only the volume of silicone particles remaining and, in that, due to its high viscosity, a great deal of force is necessary to inject the silicone dispersion through a needle of an acceptable size, whereby it is necessary for the surgeon to utilize an injection assist device to accomplish injection.

Another material that has been injected is autologous fat. This has had similar problems as the collagen, in that the body eventually breaks it down and it disappears. The act of harvesting the autologous fat and processing it for injection is also time consuming and provides variable levels of clinical improvement.

Devices have been made to attempt to overcome these problems. One device is an inflatable silicone sphere that is passed through a needle and is inflated with PVP in the same area that the other materials are injected. There are, however, some problems associated with this device. It is a delicate, mechanical device that is capable of mechanical failure of the valves, shells and structural joints. Also disadvantageous are the fixed geometry of the sphere, potential migration along the implantation tract, or extrusion of the device through the periurethral tissues.

Hydrogel particles provide desirable mechanical and tissue response properties; however they need to be resuspended in a nonaqueous carrier for injection. This allows for easy injection of small, dehydrated particles, which can later swell, in-situ following clearance of the carrier. These injectable suspensions suffer from the defect of particle settling and separation as the composition is stored for long periods of time. The settling is driven by the inherent density differences between particles and carrier. This phenomenon requires that the suspension therefore either be mixed or remixed at the time of use to obtain a uniform suspension at the time of injection. The mixing requirement is both inconvenient, can necessitate the need for additional equipment, and if not performed thoroughly can lead to uneven placement of particles when inserted into tissues, therefore possibly providing a poor procedure result. Also disadvantageous is the potential for the settled particles to clog the needle during injection. Berg, et al., in U.S. Pat. No. 5,007,940 have made an attempt to overcome the problems enumerated above by utilizing densely packed, fully hydrated hydrogel particles in disk form which deform as they pass through a needle during injection. The dense packing of the particles eliminates problems of particle settling since neighboring particles touch each other and thereby support the weight of particles above them. This art teaches that the deformability of hydrogel particles is sufficient to allow injection with dense packing (i.e., no free carrier liquid). The manufacture of the particles described in patent #5,007,940 is complex and costly and they have not been utilized commercially. Also the densely packed particles, despite their high degree of deformability, have still exhibited a relatively high viscosity whereby their use has required the use of relatively large internal diameter needles and the use of relatively large injection forces to accomplish insertion in a patient.

Van Bladel et al., in U.S. Pat. No. 5,813,411 disclose that injection of a densely packed suspension of hydrogel particles is made easier when an organic agent is added to the aqueous liquid swelling the particles. Our attempts to practice this embodiment, without the incorporation of excess suspending liquid have still presented several challenges. Most significantly, the organic additives dehydrate and shrink the particles, yet upon clearance of the dehydrating organic in the body the implant will swell to a volume larger than what was originally injected. This can cause serious problems in urethral augmentation where the additional swelling of the implant can cause closure of the urethra leading to difficulty in urination or even retention. In addition, high stresses exerted on densely packed particles as they are forced into the hub of needles during the injection process can lead to particle fracture. This is particularly significant for highly swollen hydrogels and for those exhibiting brittleness. Further dehydration of the particles by the addition of more organic either leads to particle settling when the particles become severely dehydrated or exacerbates the excess in-situ swelling of the implant or increases to required injection force. The settling also increases the opportunity of needle clogging during implantation.

Wallace et al., in U.S. Pat. No. 4,803,075 teach the addition of a polymer lubricant to an aqueous suspension of particles to reduce injection forces for injectable particulate soft tissue bulking agents. This additive to a carrier liquid does not prevent settling of particles from solution during storage and hence can still require remixing a suspension at the time of use.

Accordingly, it would be desirable to have a composition that is ready to inject at the time of use, without having to reconstitute it or use an injection assist device to inject it. Also, it would be desirable to have a composition that will not change in volume following injection, that will be soft enough so as not to cause tissue response/reaction, while still being firm enough to provide the required constriction, and that will not dissipate or migrate from the site of injection, thereby enabling the urethra to maintain the initial surgical coaptation.

SUMMARY OF THE INVENTION

The present invention provides a composition and method for augmenting, or deforming, soft tissue. The composition comprises a continuous carrier comprising an aqueous solvent having dissolved therein a hydrogel and a dehydrating agent, wherein said continuous phase is a solid at temperatures less than about 10° C. or greater than about 30° C. and is a fluid at temperatures between about 10° C. and about 30° C.; and a discontinuous phase comprising a plurality of hydrophilic hydrogel particles that are swellable in said aqueous solvent, that are not biodegradable for periods of time in excess of one year, and that have a hydrated diameter of greater than about 25 microns upon hydration by physiologic fluid, wherein a final volume of said hydrophilic hydrogel particles upon hydration by physiologic fluid is substantially the same as an initial volume of said composition.

DETAILED DESCRIPTION OF THE INVENTION

Compositions of the present invention comprise a continuous carrier phase and a discontinuous bulking phase. The discontinuous bulking phase comprises discrete, swellable, hydrophilic hydrogel particles. By swellable, it is meant that the hydrogel bulking particles are substantially insoluble in the aqueous solvent of the continuous phase, but will swell upon injection into soft tissue due to hydration by physiologic fluid from an initial dehydrated volume to a final hydrated volume that is substantially the same as the initial total volume of composition injected into the tissue to be augmented. The hydrogel bulking particles must be of a chemical composition such that they will not be broken down in the patient's body, i.e., biodegraded, for periods of time in excess of one year.

The continuous phase comprises a hydrogel carrier that is a solid, i.e., non-pouring or non-flowing, under storage conditions, e.g., under refrigeration, but becomes a pourable fluid at temperatures where the composition is to be used, e.g., at room temperature. Preferably, the hydrogel carrier is a solid at temperatures less than about 10° C. and greater than about 30° C., but becomes fluid at temperatures between about 10° C. and 30° C. The dehydrating agent is dissolved in the aqueous solvent and serves to dehydrate the hydrophilic hydrogel bulking particle. It is essential to the invention that the aqueous solvent used in the continuous phase is one in which both the hydrogel carrier is soluble and the hydrogel bulking particles are swellable.

The method of augmenting soft tissues comprises injecting a predetermined volume of the composition directly into the tissue sites requiring augmentation, e.g., bulking. The volume of the injection is injected such that coaptation of the urethral tissue is achieved. Following implantation of the composition, the hydrogel carrier and dehydrating agent are cleared by the body within six months and the hydrophilic hydrogel bulking particles remain behind to provide durable bulking. The ratio of the hydrogel carrier:dehydrating agent:hydrogel bulking particles is selected such that the final hydrated volume of hydrogel bulking particles, once hydrated with physiologic fluid, closely approximates the initial volume of composition injected into the tissue site. This is due to the use of the dehydrating agent in relative amounts effective to shrink the hydrophilic hydrogel bulking particles to a dehydrated state, relative to their hydrated volume in physiologic fluid. The mass of hydrophilic hydrogel bulking particles therefore is selected such that upon clearance of the hydrogel carrier and dehydrating agent from the site of implantation, the hydrogel bulking particles swell to replace the volume of carrier and dehydrating agent that clears the implantation site. This concept is termed a "controlled volume" injection.

The present invention provides three significant benefits over conventional augmentation compositions. First, it provides the benefit of low irritation and a good tissue mechanical compliance match through the use of hydrogel particles as the durable bulking agent. Second, the use of a hydrogel carrier that is solid under storage conditions provides the benefit of shelf stability. For example, there is no need to remix the composition at the time of use due to separation of the continuous and discontinuous phases. Thirdly, the dehydrating agent provides the benefits of easier injection into tissue, since hydrogel particle size is reduced via dehydration, and, more importantly, provides an implant that closely approximates the initial volume of composition injected. This "volume retention" property contrasts conventional injectable collagen, PTFE and silicone suspensions that provide final implanted volumes, i.e., after the respective carrier clears the sites of implantation, that are less than the initial volume of composition injected into the tissue site The hydrophilic hydrogel bulking particles, depending on the degree of dehydration, retain significant deformability so long as they retain some water. Very rigid or non-deformable particles can become difficult to inject and lead to needle clogging. It is essential that the degree of dehydration of the hydrogel bulking particles be selected to balance the benefit of reduced hydrogel particle size against the detriment of more rigid, non-deformable particles, as each property affects injectability of the dehydrated hydrogel particles. This is accomplished by utilizing an amount of dehydrating agent that is effective to provide the appropriate balance of properties.

The hydrophilic hydrogel bulking particles comprise a hydrophilic polymer network that is swellable in aqueous media. The particles are hydrophilic and absorb at least 20% of their dry mass in water, preferably over 100%. The particles are processed so as to be greater than about 25 microns in diameter in their fully hydrated state, preferably greater than 50 microns in diameter. The particles can be irregularly shaped. Hence, the diameters refer to equivalent lengths that describe the largest single dimension of particle size. It will be understood by those with ordinary skill in the art that in actual preparations there may be traces of particles outside of this size range.

Possible polymers that may be used as hydrophilic hydrogel bulking particles may be selected from the group consisting of polyethylene oxides, polypropylene oxides, polyvinyl alcohols, polyvinylpyrrolidones, polyethylene imines, polyacrylamides, polyacrylonitriles, polyHEMA polymers, Hypan polymers, starch glycolate polymers, crosslinked, acrylic acid-based polymers, (e.g., Carbopol, BFGoodrich, Charlotte, N.C.), carbohydrates and proteins. It will also be understood that derivatives of such polymers, copolymers, and/or blends or mixtures of the various polymer families may be used in this invention.

Preferred hydrogel bulking particles include radiation cross-linked polyvinylpyrrolidone (PVP). PVP is non-toxic and biocompatible. Cross-linked PVP is not known to be biodegradable and thus PVP hydrogel particles would provide bulking properties in excess of one year. While PVP in general is used in parenteral application in many medical devices and pharmaceutical formulations, we have found that PVP of a particular molecular weight range and irradiated to a particular radiation dosage exposure provides unique benefits over conventional cross-linked PVP. The use of a radiation dosage range between 5 and 7 mRAD with PVP molecular weights between 20,000 and 100,000 daltons produces a gel of optimum toughness. The lower radiation dosage range of from 2.5 to 3.3 mRAD leads to gels that are fluid and very weak. Therefore, gels cross-linked at such lower radiation dosage, while directly injectable, do not provide durable clinical correction of tissues into which they are inserted. Additionally, we have found that PVP having molecular weight over 1,000,000 daltons and being cross-linked at a radiation dosage of 10 mRAD leads to very brittle particles that are friable. The friability of these particles is problematic, since the smaller particles of PVP produced can be endocytized by cells and transported to other sites in the body.

As the composition implant is expected to provide long term tissue bulking, optimal mechanical toughness is a key physical property. When cross-linking is performed at PVP concentrations above 40% (w/w), the resulting particles, when allowed to fully hydrate, swell to such an extent that they crack and either fragment into microparticles or become mechanically weak. The preferred PVP concentration range for cross-linking is 10–20% (w/w), which produces the toughest particles in the hydrated state. It is desirable to inject the particles in a partially hydrated state since they soften upon swelling with aqueous medium. The enhanced deformability imparted to the particles in the swollen state facilitates the injection process, allowing reduced injection forces to be applied, as well as producing less trauma when the implant intrudes into injected tissues.

Dehydrating agents must be capable of shrinking the fully swollen hydrogel in physiologic medium. They must also be physiologically acceptable and capable of being cleared over time by convective, diffusional and metabolic processes normally active in body tissues. They can include organic and inorganic molecules. The dehydrating agent, at physiologically acceptable concentrations, must be capable of shrinking a fully hydrated particle by at least 10% of its volume. Examples of organic molecules that may be used as dehydrating agents with PVP hydrogel bulking particles of the present invention include polyethylene glycol, hydrophilic carbohydrates, alcohols and proteins. Inorganic salts, such as sodium carbonate or sodium phosphates, also may be used to dehydrate PVP gels. A preferred dehydrating agent is polyethylene glycol (PEG). At concentrations as low as 3% (w/w), 3,400 dalton PEG was able to shrink PVP gels by 10% in volume and at 5% concentration was able to shrink the gel by 20% in volume.

The hydrogel bulking particles are suspended in the continuous phase comprising the hydrogel carrier and the composition is packaged in a sterile syringe. As described herein, compositions according to the present invention are shelf stable, i.e., the hydrogel bulking particles do not settle out of the continuous phase comprising the hydrogel carrier upon storage. The compositions contain a uniform distribution of hydrogel bulking particles, produce a controlled volume implant and provide for injection, through acceptable needle diameters and at acceptable flow rates, with manually generated forces of less than 20 pounds, preferably of less than 10 pounds.

The benefit of shelf stability is that clinicians can directly inject the composition without further preparation, e.g., defrosting of a frozen composition, reconstitution, or mixing. This reduces procedure time and provides good assurance of sterility, as well as consistent results. Suspending the partially hydrated particles in a liquid carrier provides the desired implant volume and injection characteristics; however, the particles settle in the syringe during storage and consequently must be remixed prior to use. It was found that freezing an aqueous liquid carrier could provide shelf stability and then could be thawed and injected without further preparation. However, this is undesirable for several reasons, including that the frozen carrier required excessive time to thaw, that the particles were sometimes damaged by the expansion and contraction they were subjected to during the freezing and melting process, and that the cost and inconvenience of shipping a frozen product is prohibitive.

Surprisingly, we found that it was possible to produce carriers that could be solid, and hence shelf-stable, slightly below room temperature, and that could be rendered fluid quickly, e.g., within a few minutes, and injectable when brought to room temperature. The term solid carrier, as used herein, means those carriers that, when no deforming stresses are present and at appropriate temperatures, will suspend hydrogel bulking particles without settling for periods of over one year. The carrier also should be cleared rapidly from the body and be physiologically acceptable. Preferred carriers are soft solid hydrogels which can be made firm when refrigerated and which become soft enough to be injected when warmed a few degrees. Preferably the carrier should form a solid at 10° C. and be readily injectable at temperatures above 15° C. It should be noted that gels that become solid at temperatures above room temperature and that soften when cooled slightly (reverse thermal gels) also are included in the scope of this invention. Reverse thermal solid carriers would need to be stored above room temperature and then cooled at the time of use. Examples of polymers which are reverse thermal gels include polyethylene glycol-polypropylene glycol copolymers, which are available commercially from BASF, Mount Olive, N.J., under the trade name Pluronics. Examples of polymers exhibiting thermal gelation include polyvinyl alcohol derivatives, proteins and carbohydrates. Preferred are gelatin and iron complexed hyaluronic acid.

Gelatin is formed from denatured fibrillar collagen or tissues and can include raw material from animal, cadaver or recombinant sources. It will also be understood by those with ordinary skill in the art that other proteins and carbohydrates can be included in specific gelatin compositions. It is well established that gelatin is rapidly degraded by enzymes in the body and clears quickly following implantation.

Aqueous gelatin solutions above a critical concentration become insoluble as temperatures are reduced below 37° C. and can become solid below 10° C. This process is reversible which is a critical feature of this invention. We have found that the presence of a dehydrating agent in a gelatin solution can significantly affect its solidifying properties. Consequently, specific concentration ranges for gelatin must be selected in concert with the dehydrating agent being used. Outside of this range the benefits of rapid solidification and fluidizing within a narrow temperature range might not occur. PEG tends to make gelatin form a softer gel or requires higher gelatin concentrations to form a gel of similar firmness. At concentrations above 40% PEG we found that it was impossible to form a gelatin solid at any temperature. Hence it is critical that the dehydrating agent be present at concentrations which permit the carrier to solidify. The preferred PEG concentration range is between about 3 and about 10% with gelatin concentrations between about 1 to about 10%. Within this range there is significant shrinkage of PVP particles, yet the carrier forms a solid below 10° C. Gelatin at concentrations below about 1% in the presence of PEG (at concentrations above about 3%) did not form a solid at temperatures above 0° C. Above about 15° C., the carrier, in the desired compositional range, softens sufficiently to be easily injected. At gelatin concentrations above about 10%, the softening required for manual injection required warming to temperatures well above room temperature (20° C.). In the desired composition range, the mechanical transition occurs very rapidly at temperatures above about 15° C. and can be accomplished within a couple of minutes by grasping a syringe of 1 cm diameter or less in a human closed hand. The process requires a few more minutes if the syringe is simply allowed to sit at room temperature. We have found that at 20° C. there is no observable particle settling for periods of several days, thereby allowing sufficient time for injection following warming, without particle settling occurring.

U.S. Pat. No. 4,803,075 teaches that the addition of polymers to a carrier makes injection of the particles easier, i.e., it requires less force. The solid carriers described herein actually make injection of hydrogel particles more difficult than if they were simply immersed in water or physiologic saline (PBS—aqueous solution generally containing approximately 0.02 M sodium phosphate, 0.13 M sodium chloride adjusted to pH 7.2). The primary reason is that, unlike facilitating the injection of rigid particles as described in U.S. Pat. No. 4,803,075, hydrogel particles are highly deformable and require no lubricant to facilitate injection. It may be possible that at certain dilute concentrations of polymers preferred herein for the carrier, injection forces required for the particles may be reduced. However, at the high polymer concentrations required to make the carrier solid, injection is rendered more difficult. Increases in the injection force can be tolerated so long as they are not of such a magnitude as to make manual injection uncomfortable or require an assist device, low flow rates or overly large needles. The PVP particles preferred in this invention are sufficiently deformable to make this balance attainable. The invention will be better understood by reference to the following experimental examples.

EXAMPLE 1

PVP Particle Manufacture

A 10% (w/w) aqueous PVP solution was made using 44,000 dalton average molecular weight PVP. This solution was exposed to 5 mRad ionizing radiation from a $^{60}$Cobalt source. This produced a gel that then was rinsed thoroughly with water to remove leechable polymer and subsequently dehydrated under dry nitrogen at 40° C. The dried gel was fed through a motorized grinder and the particle size was reduced. The grindate was sieved through screens with size ranges 53–75, 75–106, 106–150, 150–212, and 212–300 microns. Analysis of fines content (particles less than 20 microns) in a microparticle analyzer revealed that the fines were reduced below 100 ppm after sufficient sieving. Approximately 40 milligrams of particles in these size ranges hydrated to bed 1 ml volume when fully equilibrated in physiologic buffer (aqueous solution of 20 mM sodium phosphate, 130 mM sodium chloride at pH 7.2). Dry particles were scattered on a microscope slide in the stage of an optical microscope and observed (measured) through a retical eyepiece. A drop of physiologic buffer was placed on the slide that hydrated the particles. The particles swelled to their final equilibrated volumes within seconds. Linear dimensions of the swollen particles were approximately 3 times larger than when dry (i.e., a 100 micron dry particle swelled to 300 microns). This is equivalent to about a 10 fold increase in particle volume.

EXAMPLE 2

Particle Dehydration by PEG

Forty (40) milligram aliquots of 106–150 micron (dry) PVP particles produced in example 1 were placed in physiologic buffer containing different concentrations of 3,400 dalton (average MW) PEG. Resulting volumes of swollen particles were measured from the bed heights in calibrated capillary tubes upon full equilibration and settling. The table below presents recorded implant volume versus PEG concentration (reported as w/w%):

| PEG content | Implant volume |
| --- | --- |
| 0% | 1.0 ml |
| 3% | 0.9 ml |
| 5% | 0.8 ml |
| 12.5% | 0.7 ml |
| 25% | 0.5 ml |
| 50% | 0.4 ml |

When the PEG containing samples were diluted with physiologic buffer, the particles swelled to 1 ml in volume.

EXAMPLE 3

Carrier Gel Production 0.8 g of collagen was dispersed in 5 ml of 0.26 M sodium hydroxide. The slurry was heated until the collagen was dissolved. 4.9 ml 0.26 M HCl was added, as was 0.03 g monobasic sodium phosphate. The pH was adjusted to 7.2 by addition of 2 drops 1 M sodium hydroxide solution. 0.5 g PEG 3,400 dalton MW was dissolved in the warm solution. The solution was poured into 3 cc syringes and refrigerated. Upon cooling, a solid (non-pourable gel formed). The gel was readily injectable at room temperature (moderate manually applied pressures) through a 22 gauge needle.

EXAMPLE 4

Viscosity Measurements of Carriers

Dynamic viscosities were measured on a Rheometrics Stress Rheometer using a cone and plate geometry. Approximately 1 ml was loaded onto 40 mm diameter, 0.4 radian cone and plate. The gap setting at the tip was 0.048 mm. Temperature was set at using a Peltier controlled plate. Viscosities were measured in oscillatory mode at a strain of 10% and at frequencies of 1 and 100 rad/s. The rheological properties of the gelatin carrier prepared in example 3 were compared with those of glycerin (used as a carrier for PTFE particles) and PVP solution (used as a carrier for silicone particles). PVP solutions at concentrations of 20, 30 and 40% (w/w), respectively, were prepared by dissolving 20, 30 and 40 grams, respectively, of PVP (BASF, Mt. Olive, N.J.—Kollidon 30, 44–54 kDa) in 80, 70 and 60 grams, respectively of deionized water.

| Composition | Viscosity (Poise) At 1 rad/sec | Viscosity (Poise) At 100 rad/sec |
| --- | --- | --- |
| Glycerol (at 10° C.) | 18.5 | 18.0 |
| Glycerol (at 20° C.) | 17.6 | 17.1 |
| 40% PVP (at 10° C.) | 8.2 | 8.0 |
| 30% PVP (at 10° C.) | 1.7 | 1.5 |
| 20% PVP (at 10° C.) | 0.7 | 0.3 |
| Gelatin Carrier at 5° C. | 760 | 82 |
| Gelatin Carrier at 10° C. | 690 | 72 |
| Gelatin Carrier at 20° C. | 42 | 0.9 |
| Gelatin Carrier at 25° C. | 13 | 0.4 |

These results show the dramatic change in fluidity of the gelatin carrier as opposed to the simple liquid carriers.

EXAMPLE 5

Measurement of Extrusion Forces

Carriers (from example 4) were loaded into 3 cc syringes (Becton Dickinson, Inc—8.5 mm ID) and extruded through 14 inches×20 gauge needles. This is the gauge and size needle commonly used with a Cystoscope for transurethral bulking agent injections. Extrusions were performed at constant plunger speed of 5.5 inches/min, corresponding to a clinically acceptable flow rate of approximately 0.14 cc/sec. The average force required to maintain this speed over 15 seconds is reported. Extrusions were performed at 20° C. Carrier compositions correspond to those reported in the viscosity measurement section.

| Carrier Composition | Maximum Extrusion Force at 5.5"/min Extrusion Speed (lb) |
| --- | --- |
| Glycerol | 40.0 |
| 40% PVP | 38.1 |
| 30% PVP | 8.2 |
| 20% PVP | 2.2 |
| Gelatin | 2.4 |

EXAMPLE 6

Measurement of PVP Particle Settling Rates

106–150 micron PVP particles from example 1 were immersed in water, 20, 30 and 40% PVP solution (example 4), as well as in glycerol and the gelatin carrier (example 3). Particles were thoroughly mixed to a uniform suspension of 125 mg particles in 14 ml of each solution. Approximately 4 ml of suspension was poured into each of three 9 mm diameter glass tubes and placed in a holder which kept the tubes vertical. The height of the column of fluid above the settling particle bed was recorded frequently over a 10 day period. At the end of 10 days the suspension was centrifuged and the height of liquid column measured. For the case of glycerol, the particles rose towards the top of the liquid rather than settled. Settling measurements were performed at 10° C. Results (separated by comas) are reported for each of 3 tubes for each liquid composition (except gelatin and glycerol) in the table below. Viscosities of the carriers correspond to those reported in the Example 4.

Note: The PVP particles swelled in glycerol as well as in the aqueous solutions.

| Elapsed Time (days) | 20% PVP solution heights (mm) | 30% PVP solution heights (mm) | 40% PVP solution heights (mm) | Glycerol Height (mm) | Gelatin Height (mm) |
| --- | --- | --- | --- | --- | --- |
| 0 | 0, 0, 0 | 0, 0, 0 | 0, 0, 0 | 0, , 0 | 0, 0 |
| 2 | 5.0, 5.0, 5.0 | 5.1, 4.7, 5.0 | 4.1, 3.5, 4.0 | 0.5, 0.5 | 0, 0 |
| 3 | 4.9, 5.1, 4.8 | 4.9, 4.8, 4.8 | 4.1, 3.7, 4.0 | 0.8, 0.8 | 0, 0 |
| 4 | 4.9, 5.0, 5.0 | 4.9, 4.8, 4.8 | 4.1, 3.7, 4.0 | 1.0, 0.9 | 0, 0 |
| 6 | 4.9, 5.1, 5.1 | 4.8, 4.8, 4.9 | 4.1, 3.71 4.0 | 1.2, 1.1 | 0, 0 |
| 9 | 4.9, 5.0, 5.1 | 5.0, 4.8, 4.8 | 4.1, 3.7, 4.0 | 1.5, 1.5 | 0, 0 |
| 10 | 5.0, 5.0, 5.1 | 4.9, 4.8, 4.8 | 4.1, 3.7, 4.0 | 1.7, 1.7 | 0, 0 |
| Height after centrifugation | 5.3, 5.3, 5.3 | 5.2, 5.3, 4.8 | 4.8, 4.3, 4.8 | 3.6, 3.8 | 0, 0 |

No particle settling was detectable in the solid gelatin, whereas in the liquid carriers settling was noticeable. Glycerol and 40% PVP were too viscous to be injected with manually applied pressures in a urethral bulking procedure (Example 5). Nevertheless, particle settling still occurred; indicating these would not be shelf stable formulations. These results also indicate that increasing the viscosity of a liquid carrier would not be sufficient to render a suspension shelf stable. In contrast, the "solid" gelatin gel prevented settling in the refrigerated state, but was easily injected at room temperature (Example 5).

EXAMPLE 7

Preparation of Tissue Bulking Implant 400 mg of particles (106–150 microns dry; from example 1) were dispersed in 10 ml carrier gel (Example 3) solution at 40° C. by stirring. The slurry was poured into 3 cc syringes and refrigerated. Upon cooling a solid gel formed with uniform particle distribution. Upon storage under refrigeration for 6 months, the particle distribution remained uniform. The system was easy to inject under manually applied pressures through a 22 gauge needle. Comparison of injected material to uninjected material under an optical microscope showed no observable change in particle sizes due to the injection process. 1 ml of implant was injected into 9 ml of physiologic buffer and shaken for 24 hours. The slurry was allowed to the settle for an additional 24 hours. The resulting particle bed volume, which settled out, was 1 ml, illustrating the controlled volume of the implant.

EXAMPLE 8

Carrier Clearance

Sterile carrier gel (example 3) samples (0.1 cc volume) were injected into rat gluteal muscles. The implanted volumes were sufficient to significantly distend the muscles into which they were injected. Animals were sacrificed after 7 days. Gross examination revealed no signs of tissue distention and detailed histologic examination showed no signs of implant present at 7 days. The muscle tissue in the injected muscles appeared normal.

EXAMPLE 9

Tissue Bulking 0.1 cc volumes of aseptically prepared tissue bulking implant (example 4) were injected through a 22 gauge needle into rat gluteal muscles. Explants were taken at 7, 14, 30, 60 and 90 days. The muscles were distended at all time periods. Histologic evaluation showed mild levels of inflammation present with no significant difference in cellularity or implant configuration at any time period.

EXAMPLE 10

Urethral Sphincter Bulking 1 cc volumes of aseptically prepared tissue bulking implant (example 4) were injected transurethrally through a 22 gauge needle using a cystoscope into canine urethras. Histologic evaluation was performed at 3, 14, 30 and 90 days. Implant boluses were present at all time periods in the injected sites and exhibited tissue distention (bulking). Histologic examination showed tissue bulking with mild levels of inflammation. No significant differences in inflammation level or implant configuration were observed between time points.

EXAMPLE 11

Gastroesophageal Sphincter Bulking

An aseptic implant was aseptically prepared similar to example 4 except using 150–212 micron particles (instead of the smaller 106–150 micron size fraction in example 4). 5 cc of material was injected through a 20 gauge needle using a laryngescope at the junction of the stomach and esophagus in a swine. Evaluation on explantation revealed bulking of the esophageal sphincter. Example 12: Hyaluronic Acid gel carrier Implant 9.5 g of $FeCl_3$ complexed 0.5% hyaluronic acid gel commercially produced under the tradename Intergel (Lifecore Biomedical, Inc.) was employed. 0.5 g of PEG 3400 was dissolved in the gel at 37° C. In 9.58 g of the resulting material (still at 37° C.), 420 mg of 106–150 micron particles (dehydrated) were dispersed. The warm dispersion was homogenized by repeated passage through a 22 gauge needle. It was then filled into 3 cc syringes and refrigerated. A stable gel formed upon refrigeration. Upon storage for 12 months a uniform particle dispersion was retained. The material was injectable through 22 gauge needles with manually applied forces.

EXAMPLE 13

Measured Extrusion Forces of PVP Particle Suspensions 420 mg of 106–150 micron (dehydrated) PVP particles (prepared in Example 1) were dispersed in 9.58 g of Hyaluronic acid gel carrier (Example 12) as well as in 9.58 g of 95/5 PBS/PEG carrier (0.5 g of 3400 dalton PEG +9.5 g PBS—deionized water containing 0.02 M dissolved sodium phosphate and 0.13 M dissolved sodium chloride adjusted to pH 7.2) and in 95/5 Hyaluronic acid/PEG solution (0.5 g PEG+9.5 g PBS containing 1% dissolved hyaluronic acid). The formulations were loaded into 3-ml syringes to a level of approximately 1.5 cc, and 14 inch long. 20 gauge needles were attached prior to measurement. The same extrusion force measurement procedure utilized in Example 5 was employed. Average Extrusion Forces for PBS was 1.5 pounds, for the 95/5 hyaluronic acid/PEG solution was 7.8 pounds and for the iron complexed hyaluronic acid gel (Example 12) was 6.3 pounds. This result shows that the addition of dissolved polymer to the hydrogel particle suspensions actually makes extrusion more difficult than when the particles are dispersed in water/PBS. It also shows that extrusion was not made so much more difficult that it was still below 10 pounds-force and could therefore still be performed manually without an assist device.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A composition, comprising:
   a continuous phase comprising an aqueous solvent having dissolved therein a hydrogel solid carrier and a dehydrating agent in relative amounts effective to render said solid carrier solid at temperatures less than about 10° C. or greater than about 30° C. and fluid at temperatures between about 10° C. and about 30° C.; and
   a discontinuous phase comprising a plurality of hydrophilic hydrogel particles that are swellable in said aqueous solvent, that are not biodegradable for periods of time in excess of one year, and that have a hydrated diameter of greater than about 25 microns upon hydration by physiologic fluid, wherein a final volume of said hydrophilic hydrogel particles upon hydration by physiologic fluid is substantially the same as an initial volume of said composition.

2. The composition of claim 1 wherein said hydrophilic hydrogel is selected from the group consisting of polyethylene oxides, polyvinyl alcohol's, polyvinylpyrrolidones, polyethylene imines, polyacrylamides, polyacrylonitriles, polyHEMA polymers, Hypan polymers, starch glycolate polymers, carbopol polymers, carbohydrates and proteins.

3. The composition of claim 2 wherein said hydrophilic hydrogel particles comprise polyvinylpyrrolidone particles prepared from polyvinylpyrrolidone of molecular weight between about 20,000 and 100,000 daltons and that have been cross-linked by a radiation dosage of between about 5 and 7 mRad.

4. The composition of claim 3 wherein the diameter of said fully hydrated polyvinylpyrrolidone particles is greater than about 50 microns.

5. The composition of claim 1 wherein said hydrophilic hydrogel particles absorb at least 20 percent of their dry mass in water.

6. The composition of claim 1 wherein said hydrophilic hydrogel particles absorb at least 100 percent of their dry mass in water.

7. The composition of claim 1 wherein said dehydrating agent comprises polyethylene glycol having a molecular weight of about 3,400 daltons.

8. The composition of claim 3 wherein said dehydrating agent comprises polyethylene glycol having a molecular weight of about 3,400 daltons.

9. The composition of claim 8 wherein said continuous phase comprises gelatin or an iron-complexed hyaluronic or acrylic acid as said hydrogel.

10. The composition of claim 9 comprising from about 1 to about 10 weight percent of said gelatin, from about 3 to about 10 weight percent of said polyethylene glycol, and from about 3 percent to about 5 percent of said polyvinylpyrrolidone hydrogel particles.

11. A method of augmenting soft tissue, comprising:
   determining an initial volume of a composition to be injected into soft tissue to be augmented, said composition comprising:
      a continuous phase comprising an aqueous solvent having dissolved therein a hydrogel solid carrier and a dehydrating agent in relative amounts to render said solid carrier solid at temperatures less than about 10° C. and greater than about 30° C. and fluid at temperatures between about 10° C. and about 30° C.; and
      a discontinuous phase comprising a plurality of hydrophilic hydrogel particles that are swellable in said aqueous solvent, that are not biodegradable for periods of time in excess of one year, and that have a hydrated diameter of greater than about 25 microns upon hydration by physiologic fluid, wherein a final volume of said hydrophilic hydrogel particles upon hydration by physiologic fluid is substantially the same as an initial volume of said composition; and
      injecting the initial volume of the composition into the soft tissue.

12. The method of claim 11 wherein said hydrophilic hydrogel is selected from the group consisting of polyethylene oxides, polyvinyl alcohols, polyvinylpyrrolidones, polyethylene imines, polyacrylamides, polyacrylonitriles, polyHEMA polymers, Hypan polymers, starch glycolate polymers, carbopol polymers, carbohydrates and proteins.

13. The composition of claim 12 wherein said hydrophilic hydrogel particles comprise polyvinylpyrrolidone particles prepared from polyvinylpyrrolidone of molecular weight between about 20,000 and 100,000 daltons and that have been cross-linked by a radiation dosage of between about 5 and 7 mRAD.

14. The method of claim 11 wherein said dehydrating agent comprises polyethylene glycol having a molecular weight of about 3,400 daltons.

15. The method of claim 13 wherein said dehydrating agent comprises polyethylene glycol having a molecular weight of about 3,400 daltons.

16. The method of claim 15 wherein said continuous phase comprises gelatin or an iron-complexed hyaluronic acid as said hydrogel.

17. The method of claim 16 comprising from about 1 to about 10 weight percent of said gelatin, from about 3 to about 10 weight percent of said polyethylene glycol, and from about 3 percent to about 5 percent of said polyvinylpyrrolidone hydrogel particles.

* * * * *